United States Patent
Srivastava

(12) 
(10) Patent No.: US 6,468,540 B1
(45) Date of Patent: *Oct. 22, 2002

(54) IMMUNOTHERAPEUTIC STRESS PROTEIN-PEPTIDE COMPLEXES AGAINST CANCER

(75) Inventor: Pramod K. Srivastava, Avon, CT (US)

(73) Assignee: Mount Sinai School of Medicine of New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/489,218

(22) Filed: Jan. 21, 2000

Related U.S. Application Data

(63) Continuation of application No. 09/061,365, filed on Apr. 16, 1998, now Pat. No. 6,017,544, which is a division of application No. 08/315,892, filed on Sep. 30, 1994, now Pat. No. 5,750,119, which is a continuation-in-part of application No. 08/180,685, filed on Jan. 13, 1994, now Pat. No. 5,997,873.

(51) Int. Cl.[7] .................. A61K 39/00; A61K 39/385; A61K 45/00; A61K 38/00

(52) U.S. Cl. .................. 424/193.1; 424/193.1; 424/277.1; 424/185.1; 424/195.11; 424/85.1; 514/21; 530/300

(58) Field of Search .................. 424/193.1, 277.1, 424/185.1, 195.11, 192.1, 85.1; 514/21; 530/300

(56) References Cited

U.S. PATENT DOCUMENTS

| | | |
|---|---|---|
| 4,690,915 A | 9/1987 | Rosenberg |
| 5,188,964 A | 2/1993 | McGuire et al. |
| 5,232,833 A | 8/1993 | Sanders et al. |
| 5,288,639 A | 2/1994 | Burnie et al. |
| 5,348,945 A | 9/1994 | Berberian et al. |
| 5,750,199 A | 5/1998 | Srivastava |
| 5,830,464 A | 11/1998 | Srivastava |
| 5,837,251 A | 11/1998 | Srivastava |
| 5,935,576 A | 8/1999 | Srivastava |
| 5,961,979 A | 10/1999 | Srivastava |
| 5,985,270 A | 11/1999 | Srivastava |
| 5,997,873 A | 12/1999 | Srivastava |
| 6,017,544 A | 1/2000 | Srivastava |
| 6,030,618 A | 2/2000 | Srivastava |
| 6,048,530 A | 4/2000 | Srivastava |

FOREIGN PATENT DOCUMENTS

| | | |
|---|---|---|
| GB | 2 251 186 A | 7/1992 |
| WO | WO 89/12455 | 12/1989 |
| WO | WO 90/02564 | 3/1990 |
| WO | WO 91/15572 | 10/1991 |
| WO | WO 92/01717 | 2/1992 |
| WO | WO 92/08484 | 5/1992 |
| WO | WO 92/08488 | 5/1992 |
| WO | WO 93/14118 | 7/1993 |
| WO | WO 93/17712 | 9/1993 |
| WO | WO 93/18146 | 9/1993 |
| WO | WO 93/18147 | 9/1993 |
| WO | WO 93/18150 | 9/1993 |
| WO | WO 93/21529 | 10/1993 |
| WO | WO 93/24136 | 12/1993 |
| WO | WO 94/03208 | 2/1994 |
| WO | WO 94/03599 | 2/1994 |
| WO | WO 94/04676 | 3/1994 |
| WO | WO 94/11513 | 5/1994 |

OTHER PUBLICATIONS

U.S. patent application Ser. No. 08/462,395, Srivastava et al., filed Jun. 5, 1995.

Aldovini et al. (1992) "The New Vaccines", *Technology Review* pp. 24–31.

Barrios et al. (1992) "Mycobacterial heat–shock proteins as carrier molecules. II: The use of the 70–kDa mycobacterial heat–shock protein as carrier for conjugated vaccines that can circumvent the need for adjuvants and Bacillus Calmette Guérin priming", *Eur. J. Immunol.* 22:1365–1372.

Barrios et al. (1994) "Specificity of antibodies induced after immunization of mice with the mycobacterial heat shock proteins of 65 kD", *Clin. Exp. Immunol.* 98:224–228.

Barrios et al. (1994) "Heat shock proteins as carrier molecules: in vivo helper effect mediated by *Escherichia coli* GroEL and DnaK proteins requires cross–linking with antigen", *Clin. Exp. Immunol.* 98:229–233.

Basombrio (1970) "Search for common antigenicities among twenty–five sarcomas induced by methylcholanthrene", *The Institute for Cancer Research* 30:2458–2462.

Bensaude et al. (1983) "Spontaneous high expression of heat–shock proteins in mouse embryonal carcinoma cells and ectoderm from day 8 mouse embryo", *EMBO J.* 2:173–177.

Blachere et al. (1993) "Heat Shock Protein Vaccines Against Cancer," *Journal of Immunotherapy* 14:352–356.

Blachere and Srivastava (1993) "Immunization with GP96 heat shock proteins isolated from tumors or influenza virus infected cells elicits MHC–restricted, antigen–specific cytotoxic T lymphocytes against the corresponding cells", *J. Cellular Biochem. Keystone Symposia* NZ502, p. 124.

(List continued on next page.)

*Primary Examiner*—Geetha P. Bansal
(74) *Attorney, Agent, or Firm*—Pennie & Edmonds LLP

(57) ABSTRACT

Disclosed is a method for inhibiting the proliferation of a tumor in a mammal. The method involves the steps of (a) isolating a stress protein-peptide complex from tumor cells previously removed from the mammal and (b) administering the isolated stress protein-peptide complex back to the mammal in order to stimulate in the mammal an immune response against the tumor from which the complex was isolated. Stress protein-peptide complexes having particular utility in the practice of the instant invention include the Hsp70-peptide, Hsp90-peptide and gp96-peptide complexes.

17 Claims, No Drawings

OTHER PUBLICATIONS

Boon (1992) "Toward a genetic analysis of tumor rejection antigens", *Advances in Cancer Research* 58:177–210.

Cohen (1993) "Cancer Vaccines Get A Shot In the Arm", *Science* 262:841–843.

Craig (1993) "Chaperones: Helpers Along the Pathways to Protein Folding", *Science* 260:1902–1904.

Ebert (1987) "Characterization of an immunosuppressive factor derived from colon cancer cells", J. Immunol., 138(7):2161–2168.

Elliot et al. (1990) "Naturally Processed Peptides", *Nature* 348:195–197.

Falk et al. (1991) "Allele–specific Motifs Revealed by Sequencing of Self–peptides Eluted from MHC Molecules", *Nature* 351:290–296.

Falk et al. (1990) "Cellular Peptide Composition Governed by Major Histocompatibility Complex Class I Molecules", *Nature* 348:248–251.

Fedweg and Srivastava (1993) "Evidence for biochemical heterogeneity of gp96 heat shock protein/tumor rejection antigen", Mont Sinai School of Medicine NZ 206, p. 108.

Flynn et al. (1989) "Peptide binding and release by proteins implicated as catalysts of protein assembly", *Science* 245:385–390.

Flynn et al. (1991) "Peptide–binding Specificity of the Molecular Chaperone BiP", *Nature* 353:726–730.

Franklin (1993) "Making vaccines fit the cancer", *New Scientist* 140:17.

Gething et al. (1992) "Protein Folding in the Cell", *Nature* 355:33–45.

Globerson and Feldman (1964) "Antigenic specificity of benzo[a]pyrene–induced sarcomas", *Journal of the National Cancer Institute* 32(6):1229–1242.

Heike et al. (1994) "Protective cellular immunity against a spontaneous mammary carcinoma from ras transgenic mice," Immunobiology 190(4–5):411–423.

Huber et al. (1982) "Protease inhibitors interfere with the transforming growth factor–β–dependent but not the transforming growth factor–β–independent pathway of tumor cell–mediated immunosuppression", J. Immunol. 148(1):277–284.

Jakob et al. (1993) "Small Heat Shock Proteins Are Molecular Chaperones", *J. Biol. Chem.* 268:1517–1520.

Jardetzky et al. (1991) "Identification of Self Peptides Bound to Purified HLA–B27", *Nature* 253:326–329.

Lakey et al (1987) "Identification of a peptide binding protein that plays a role in antigen presentation", *Proc. Natl. Acad. Sci. USA* 84:1659–1663.

Lanzavecchia (1993) "Identifying Strategies for Immune Intervention", *Science* 260:937–944.

Levinson et al. (1979) "Metal Binding Drugs Induce Synthesis of Four Proteins in Normal Cells ", *Biol Trace Element Research* 1:15–23.

Lévy (1991) "ATP is Required for In Vitro Assembly of MHC Class I Antigens but Not for Transfer of Peptides across the ER Membrane", *Cell* 67:265–274.

Li et al. (1994) "A critical contemplation on the role of heat shock proteins in transfer of antigenic peptides during antigen presentation", Behring Institute Mutteliungen 94:37–47.

Li and Srivastava (1993) "Tumor rejection antigen gp96/grp94 is an ATPase: Implications for protein folding and antigen presentation", *EMBO J.* 12(8):3143–3151.

Lindquist and Craig (1988) "The heat–shock proteins", *Ann. Rev. Genet.* 22:631–677.

Luescher et al. (1991) "Specific Binding of Antigenic Peptides to Cell–associated MHC Clas I Molecules", *Nature* 351:72–77.

Lukacs et al. (1993) "Tumor cells transfected with a bacterial heat–shock gene lose tumorigenicity and induce protection against tumors", *J. Exp. Med.* 178:343–348.

Lussow et al. (1991) "Mycobacterial heat–shock proteins as carrier molecules", *Eur. J. Immunol.* 21:2297–2302.

Madden et al. (1991) "The Structure of HLA–B27 Reveals Nonamer Self–peptides Bound in an Extended Conformation", *Nature* 353:321–325.

Maki et al. (1993) "Mapping of the Genes for Human Endoplasmic Reticular Heat Shock Protein gp96/grp94", *Somatic Cell Mol. Genetics* 19(1):73–81.

Maki et al. (1990) "Human homologue of murine tumor rejection antigen gp96: 5'–Regulatory and coding regions and relationship to stress–induced proteins", *Proc. Natl. Acad. Sci. USA* 87:5658–5663.

McCall et al. (1989) "Biotherapy: A New Dimension in Cancer Treatment", *Biotechnology* 7:231–240.

Melnick (1985) "Virus Vaccines: An Overview", Proceedings of the First Annual Southwest Foundation for Biomedical Research International Symposium, Houston, Texas, Nov. 8–10, 1984, *American Society for Microbiology* pp. 1–13.

Mizoguchi et al. (1982) "Alternation in signal transduction molecules in T lymphocytes from tumor–bearing mice", Science 258:1795–1798.

Nelson et al. (1992) "The Translation Machinery and 70 kd Heat Shock Protein Cooperate in Protein Synthesis", *Cell* 71:97–105.

Palladino et al. (1987) "Expression of shared tumor–specific antigen by two chemically induced BALB/c sarcomas", *Cancer Research* 47:5074–5079.

Prehn and Main (1957) "Immunity to methylcholanthrene–induced sarcomas", *Journal of the National Cancer Institute* 18(6):769–778.

Rothman (1989) "Polypeptide Chain Binding Proteins: Catalysts of Protein Folding and Related Processes in Cells", *Cell* 59:591–601.

Rötzschke et al. (1990) "Isolation and Analysis of Naturally Processed Viral Peptides as Recognized by Cytotoxic T cells", *Nature* 348:248–251.

Salk et al. (1993) "A Strategy for Prophylactic Vaccination Against HIV", *Science* 260:1270–1272.

Schumacher et al. (1991) "Peptide Selection by MHC Class I Molecules", *Nature* 350:703–706.

Srivastava et al. (1991) "Protein Tumor Antigens", *Curr. Opin. Immunol.* 3:654–658.

Srivastava et al. (Mar. 1993) "Evidence for peptide–chaperoning by the endoplasmic reticular heat shock protein GP96: Implications for vaccination against cancer and infectious diseases", *J Cell Biochem Suppl* 17D:94 (Abstract NZ014).

Srivastava et al. (1984) "The Serologically Unique Cell Surface Antigen of Zajdela Ascitic Hepatoma is also its Tumor–Associated Transplantation Antigen", *Int. J. Cancer* 33:417–422.

Srivastava et al. (1989) "Identification of a Human Homologue of the Murine Tumor Rejection Antigen GP96," *Cancer Res.* 49:1341–1343.

Srivastava et al. (1988) "Individually Distinct Transplantation Antigens of Chemically Induced Mouse", *Immunology Today* 9:78–83.

Srivastava et al. (1987) "5'–Structural analysis of genes encoding polymorphic antigens of chemically induced tumors", *Proc. Natl. Acad. Sci. USA* 84:3807–3811.

Srivastava et al. (1993) "Peptide–Binding Heat Shock Proteins in the Endoplasmic Reticulum: Role in Immune Response to Cancer and in Antigen Presentation", *Advances in Cancer Research* 62:153–177.

Srivastava and Maki (1991) "Stress–induced proteins in immune response cancer", *Microbiol. Immunol.* 167:109–123.

Srivastava and Heike (1986) "Tumor–specific immunogenicity of stress–induced proteins: Convergence of two evolutionary pathways of antigen presentation?", *Seminars in Immunology* 3:57–64.

Srivastava et al. (1986) "Tumor rejection antigens of chemically induced sarcomas of inbred mice", *Proc. Natl. Acad. Sci. USA* 83:3407–3411.

Srivastava (1991) "Tumor–specific Immunogenicity of Stress–induced Proteins: Covergence of Two Evolutionary Pathways of Antigen Presentation?", Semin Immunol. Jan. 1991;3(1):57–64.

Srivastava et al. (1994) "Heat Shock Proteins Transfer Peptides During Antigen Processing and CTL Priming", Immunogenetics 39:93–98.

Subbarao et al. (1992) "A General Overview of Viral Vaccine Development," *Genetically Engineered Vaccines* 327:51–57.

Szikora et al. (1990) "Structure of the gene of tum–transplantation antigen P35B presence of a point mutation in the antigenic allele", *EMBO J.* 9(4):1041–1050.

Thomas et al. (1982) "Molecular and Cellular Effects of Heat Shock and Related Treatments of Mammalian Tissue–Culture Cells", *Cold Spring Harbor Symp Quant Biol* 46:985–996.

Udono (1993) "Heat shock proteins HSP70, HSP90 and GP96 elicit tumor specific immunity to the tumors from which they are isolated", *J. Cell. Biochem.* Suppl. 17D:113 (Abstract NZ225).

Udono et al. (1993) "Heat Shock Protein 70–associated Peptides Elicit Specific Cancer Immunity", *J. Exp. Med.* 178:1391–1396.

Udono et al. (1994) "Comparison of Tumor–Specific Immunogenicities of Stress–Induced Proteins gp96, hsp90, and hsp70", *J. Immunol.* 152:5398–5403.

Udono et al. (1994) "Cellular requirements for tumor–specific immunity elicited by heat shock proteins: Tumor rejection antigen gp96 primes CD8+ T cells in vivo", *Proc. Natl. Acad. Sci. (USA)* 91:3077–3081.

Ullrich et al. (1986) "A mouse tumor–specific transplantation antigen is a heat shock–related protein", *Proc. Natl. Acad. Sci. USA* 83:3121–3125.

Vanbuskirk et al. (1989) "Peptide binding protein having a role in antigen presentation is a member of the hsp70 heat shock family", *J. Exp. Med.* 170:1799–1809.

Van den Enyde et al. (1991) "The gene coding for a major tumor rejection antigen of tumor P815 is identical to the normal gene of syngeneic DBA/2 mice", J. Exp. Med. 173:1373–1384.

Vitanen et al. (1992) "Mammalian Mitochondrial Chaperonin 60 Functions as a single Toroidal Ring", J. Biol. Chem. 267:695–698.

Welch et al. (1982) "Purification of the Major Mammalian Heat Shock Proteins", *J. Biol. Chem.* 257:14949–14959.

Welch et al. (1985) "Rapid Purification of Mammalian 70,000–Dalton Stress Proteins: Affinity of the Proteins for Nucleotides", *Mol. Cell. Biol.* 5:1229–1237.

Welch (1993) "How Cells Respond to Stress", *Scientific American* pp. 56–64.

Young (1990) "Stress Proteins and Immunology", *Annu. Rev. Immunol.* 8:401–420.

Yu et al. (1991) "Sequence Analysis of Peptides Bound to MHC Class II Molecules", *Nature* 353:622–627.

U.S. patent application Ser. No. 09/412,420, Srivastava, filed Oct. 5, 1999.

U.S. patent application Ser. No. 09/454,734, Srivastava, filed Dec. 6, 1999.

U.S. patent application Ser. No. 09/657,722, Srivastava, filed Sep. 8, 2000.

Maki (1991) "The Human Homologue of the Mouse Tumor Rejection Antigen GP96", Ph.D. thesis, Cornell University.

Srivastava and Old (1989) "Gp96 Molecules: Recognition Elements in Tumor Immunity", *Human Tumor Antigens and Specific Tumor Therapy*, pp. 63–71.

Srivastava et al. (1990) "Immunization with Soluble Gp96 Antigens Elicits Tumor–Specific Cellular Immunity", *Cellular Immunity and the Immunotherapy of Cancer*, pp. 307–314.

IMMUNOTHERAPEUTIC STRESS PROTEIN-PEPTIDE COMPLEXES AGAINST CANCER

This is a continuation of application Ser. No. 09/061,365 filed Apr. 16, 1998, now U.S. Pat. No. 6,017,544, which is a division of application Ser. No. 08/315,892 filed Sep. 30, 1994, now U.S. Pat. No. 5,750,119, each of which is incorporated by reference herein in its entirety, which is a C-I-P of Ser. No. 08/180,685 filed Jan. 13, 1994 U.S. Pat. No. 5,997,873.

FIELD OF THE INVENTION

The application relates generally to the field of cancer therapy, in particular, to the immunotherapy of human cancer.

BACKGROUND OF THE INVENTION

It has been found that inbred mice and rats can be immunized phrophylactically against tumors derived from mice and rats of the same genetic background (Gross (1943) Cancer Res. 3:323–326; Prehn et al. (1957) J. Natl. Cancer Inst. 18:769–778; Klein et al. (1960) Cancer Res. 20:1561–1572; Old et al. (1962) Ann NY Acad. Sci. 101:80–106; for review, see Srivastava et al. (1988) Immunology Today 9:78–83). These studies not only showed that mice vaccinated with inactivated cancer cells become immunized against subsequent challenges of live cancer cells but also demonstrated the existence of tumor-specific antigens.

Further studies revealed that the phenomenon of prophylactically induced immunity is tumor-specific. Although mice can be specifically immunized against the tumor cells that were used to immunize them they still remain sensitive to challenges with other unrelated tumors (Basombrio (1970) Cancer Res. 30:2458–2462, Globerson et al. (1964) J. Natl. Cancer Inst. 32:1229–1243). The demonstration of immunogenicity of cancer cells led to a search for the cancer-derived molecules which elicit resistance to tumor challenges. The general approach was to fractionate cancer cell-derived proteins and test them individually for their ability to immunize mice against the cancers from which the fractions were prepared (see Srivastava et al. (1988) supra; Old (1981) Cancer Res. 41:361–375). A number of proteins have been identified by this method, however, a large proportion of these proteins are related to a class of proteins known as stress-induced proteins or stress proteins (Lindquist et al. (1988) Annual Rev. Genet. 22:631–677). Because the stress proteins are among the most highly conserved and abundant proteins in nature, they are unlikely candidates for tumor specific antigens. Stress proteins have subsequently been shown to non covalently associate with a variety of peptides thereby to form stress protein-peptide complexes (Gething et al. (1992) Nature 355:33–45; Lindquist et al. (1988) supra; Young (1990) Annu. Rev. Immunol. 8:401–420; Flynn et al. 1991) Nature 353:726–730).

Studies have also shown that stress protein-peptide complexes lose their immunogenicity upon treatment with ATP (Udono et al. (1993) J. Exp. Med. 178:1391–1396). This treatment is known to dissociate the stress-protein peptide complex into its stress protein and peptide components. Considering that there are no differences in the structure of stress proteins derived from normal and tumor cells, and that stress proteins bind a wide spectrum of peptides in an ATP dependent manner it appears that the antigenicity of the stress protein-peptide complex results not from the stress protein per se, but from the peptide associated with the stress protein.

One of the major conceptual difficulties in cancer immunotherapy has been the possibility that human cancers, like cancers of experimental animals, are antigenically distinct. Clearly, there is some recent evidence for existence of common tumor antigens (Kawakami et al. (1992) J. Immunol. 148:638–643; Darrow et al. (1989) J. Immunol. 142:3329–3334), and this augurs well for prospects of cancer immunotherapy. Nonetheless, in light of the overwhelming evidence from experimental and human systems, it is reasonable to assume that at the very least, human tumors would show tremendous antigenic diversity and heterogeneity.

The prospect of identification of the immunogenic antigens of individual tumors from cancer patients (or even of 'only' several different types of immunogenic antigens in case the antigens are shared), is daunting to the extent of being impractical. Conventional cancer therapies typically are based on the isolation and characterization of specific antigenic determinants which then may become the target for subsequent immunotherapies. In addition, although studies have demonstrated that mammals can be immunized prophylactically against tumors derived from mammals of the same genetic background, heretofore it has not been appreciated that a mammal harboring a tumor can be therapeutically immunized with a composition derived from its own tumor as a means of treating a cancer preexisting in the mammal.

Accordingly, it is an object of the instant invention to provide a novel method for therapeutically inhibiting proliferation of tumors in a mammal. The method described herein does not require the isolation and characterization of specific antigenic determinants, and accordingly provides a more rapid approach for making and using immunogenic compositions effective in inhibiting the proliferation of specific predetermined tumors in mammals.

This and other objects and features of the invention will be apparent from the description and claims which follow.

SUMMARY OF THE INVENTION

The observation that stress proteins chaperone the antigenic peptides of the cells from which they are derived provides an approach for readily isolating antigenic peptides for a preselected tumor. Once isolated, the stress protein-peptide complexes are administered back to the animal from which they were derived in order to elicit an immune response against a preexisting tumor. Accordingly, this approach circumvents the necessity of isolating and characterizing specific tumor antigens and enables the artisan to readily prepare immunogenic compositions effective against a preselected tumor.

In its broadest aspect, the invention provides a method for inhibiting proliferation of a preselected tumor in a mammal. The method comprises administering to the mammal undergoing therapy a composition comprising a pharmaceutically acceptable carrier in combination with a stress protein-peptide complex. The complex having been isolated from a tumor cell previously excised from the mammal and characterized in that it is operative to initiate in the mammal an immune response against the tumor cells from which it was derived. The complex subsequently is administered back to the mammal in an amount sufficient to elicit in the mammal an immune-response against the tumor cells thereby to inhibit proliferation of any tumor cells still remaining in the mammal.

It is contemplated that this approach may be used in combination with other conventional cancer therapies which include, for example, surgery, radiation therapy and chemotherapy. For example, following surgical excision of cancerous tissue the artisan, using the principles described herein, may isolate stress protein-peptide complexes from the excised tissue and administer the complex back to the mammal. The complex subsequently induces a specific immune response against any remaining tumor cells that were not excised during surgery. The approach is amenable to cancer therapy when the primary tumor has metastasized to different locations with the body.

The term "tumor" as used herein, is understood to mean any abnormal or uncontrolled growth of cells which may result in the invasion of normal tissues. It is contemplated also that the term embraces abnormal or uncontrolled cell growths that have metastasized, i.e., abnormal cells that have spread from a primary location in the body (i.e., primary tumor) to a secondary location spatially removed from the primary tumor.

The term "stress protein" as used herein, is understood to mean any cellular protein which satisfies the following criteria. It is a protein whose intracellular concentration increases when a cell is exposed to stressful stimuli, is capable of binding other proteins or peptides, and is capable of releasing the bound proteins or peptides in the presence of adenosine triphosphate (ATP) and/or low pH. Stressful stimuli include, but are not limited to, heat shock, nutrient deprivation, metabolic disruption, oxygen radicals, and infection with intracellular pathogens.

The first stress proteins to be identified were the heat shock proteins (Hsp's). As their name suggests, Hsp's typically are induced by a cell in response to heat shock. Three major families of mammalian Hsp's have been identified to date and include Hsp60, Hsp70 and Hsp90. The numbers reflect the approximate molecular weight of the stress proteins in kilodaltons. The members of each of the families are highly conserved, see for example, Bardwell et al. (1984) *Proc. Natl. Acad. Sci.* 81:848–852; Hickey et al. (1989) *Mol. Cell Biol.* 9:2615–2626; Jindal (1989) *Mol. Cell. Biol.* 9:2279–2283, the disclosures of which are incorporated herein by reference. Members of the mammalian Hsp90 family identified to date include cytosolic Hsp90 (also known as Hsp83) and the endoplasmic reticulum counterparts Hsp90 (also known as Hsp83), Hsp87, Grp94 (also known as ERp99) and gp96. See for example, Gething et al. (1992) *Nature* 355:33–45 the disclosure of which is incorporated herein by reference. Members of the Hsp70 family identified to date include: cytosolic Hsp70 (also known as p73) and Hsc70 (also known as p72); the endoplasmic reticulum counterpart BiP (also known as Grp78); and the mitochondrial counterpart Hsp 70 (also known as Grp75), Gething et al. (1992) supra. To date, members of the mammalian Hsp60 family have only been identified in the mitochondria, Gething et al. (1992) supra.

In addition, it has been discovered that the Hsp-60, Hsp-70 and Hsp-90 families are composed of proteins related to the stress proteins in amino acid sequence, for example, having greater than 35% amino acid identity, but whose expression levels are not altered by stressful stimuli. Accordingly, it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are stimulated in response to stressful stimuli.

The term "peptide", as used herein, is understood to mean any amino acid sequence isolated from a mammalian tumor cell in the form of a stress protein-peptide complex.

The term "immunogenic stress protein-peptide complex", as used herein, is understood to mean any complex which can be isolated from a mammalian tumor cell and comprises a stress protein non covalently associated with a peptide. The complex is further characterized in that it is operative to induce in the mammal an immune response against the tumor cells from which the complex was derived.

The term "immune response" is understood to mean any cellular process that is produced in the mammal following stimulation with an antigen and is directed toward the elimination of the antigen from the mammal. The immune response typically is mediated by one or more populations of cells characterized as being lymphocytic and/or phagocytic in nature.

In a more specific aspect of the invention, the stress protein in the stress protein-peptide complex is selected from the group consisting of Hsp70, Hsp90 and gp96. Stress protein-peptide complexes which include Hsp70-peptide, Hsp90-peptide and gp96-peptide complexes may be isolated simultaneously from a batch of tumor cells excised from a mammal. During immunotherapy it is contemplated that one or more of the aforementioned complexes may be administered to the mammal in order to stimulate the optimal immune response against the tumor.

It is contemplated that the method described herein is particularly useful in the treatment of human cancer. However, it is contemplated that the methods described herein likewise will be useful in immunotherapy of cancers in other mammals, for example, farm animals (i.e., cattle, horses, goats, sheep and pigs) and household pets (i.e., cats and dogs).

In another aspect of the invention, it is contemplated that the immune response is effected by means of a T cell cascade, and more specifically by means of a cytotoxic T cell cascade. The term "cytotoxic T cell", as used herein, is understood to mean any T lymphocyte expressing the cell surface glycoprotein marker CD8 that is capable of targeting and lysing a target cell which bears a class I histocompatibility complex on its cell surface and is infected with an intracellular pathogen.

In another aspect of the invention, the stress protein-peptide complexes may be administered to the mammal in combination with a therapeutically active amount of a cytokine. As used herein, the term "cytokine" is meant to mean any secreted polypeptide that influences the function of other cells mediating an immune response. Accordingly, it is contemplated that the complex can be coadministered with a cytokine to enhance the immune response directed against the tumor. Preferred cytokines include, but are not limited to, interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interferon α (IFNα), interferon β (IFNβ), interferon γ (IFNγ), tumor necrosis factor α (TNF ), tumor necrosis factor β (TNFβ), granulocyte colony stimulating factor (G-CSF), granulocyte/macrophage colony stimulating factor (GM-CSF), and transforming growth factor β (TGF-β).

The complex may be administered to a mammal when combined with a conventional pharmaceutically acceptable carrier, adjuvant, or excipient using techniques well known in the art. The dosage and means of administration of the family of stress protein-peptide complexes necessarily will depend upon a variety of factors such as the stability of the complex under physiological conditions, the effectiveness of the complex at eliciting an immune response, the size and distribution of the tumor, and the age, sex and weight of the mammal undergoing therapy.

Typically, the complex should be administered in an amount sufficient to initiate in the mammal an immune response against the tumor from which the complex was derived and in an amount sufficient to inhibit proliferation of the tumor cells in the mammal. The amount of stress protein-peptide complex administered preferably is in the range of about 1–1000 micrograms of complex/kg body weight of the mammal/administration, and most preferably about 100–250 micrograms of complex/kg body weight of the mammal/administration. It is contemplated that typical dose will be in the range of about 5 to about 20 mg for a human subject weighing about 75 kg. In addition, it is contemplated that the strength of the immune response may be enhanced by repeatedly administering the complex to the individual. The mammal preferably receives at least two doses of the stress protein-peptide complex at weekly intervals. If necessary, the immune response may be boosted at a later date by subsequent administration of the complex. It is contemplated, however, that the optimal dosage and immunization regimen may be found by routine experimentation by one skilled in the art.

DETAILED DESCRIPTION

The invention is based on the observation that stress protein-peptide complexes chaperone antigenic peptides of the cells from which they are derived. Conventional cancer therapies are based upon the isolation an characterization of tumor specific antigens which then become the target for a specific therapeutic regime. Because of the antigenic diversity of mammalian cancers the isolation and characterization of specific tumor antigens for each specific tumor can be impractical. The instant invention thus provides an alternative approach to cancer immunotherapy by obviating the necessity of isolating and characterizing tumor specific antigens for each tumor being treated.

The invention described herein provides a method for inhibiting proliferation of a preselected tumor in a mammal. The method comprises isolating or obtaining tumor cells from the mammal undergoing therapy. This is accomplished readily using conventional surgical procedures well known in the art. Typically, tumor cells are excised from the mammal during routine surgical recision of the tumor. The method then involves isolating stress protein-peptide complexes from the excised tumor cells. This is accomplished using any one of the isolation procedures described in detail herein below. The stress protein-peptide complexes are characterized in that when they are administered back to the mammal they are capable of initiating a specific immune response against the same type of tumor cells that they were derived from. Finally, the method comprises the step of administering back to the mammal the isolated stress protein-peptide complex in an amount sufficient to elicit in the mammal an immune response against the tumor cells thereby inhibiting proliferation of any tumor cells remaining in the mammal.

It is contemplated that this approach may be used in combination with one or more conventional cancer therapies which include, for example, surgery, radiation therapy and chemotherapy. For example, following surgical excision of cancerous tissue the artisan, using the principles described herein, may isolate stress protein-peptide complexes from the excised tissue and administer the complex back to the mammal. The complex then induces in the mammal a specific immune response against any tumor cells that were not removed during surgery. Alternatively, the method described herein provides a novel approach for treating cancer when the primary tumor has metastasized to multiple locations with the body. For example, when the cancer has metastasized, making surgical intervention impractical, a stress protein-peptide complex may be used either alone or in combination with another standard chemotherapeutic agent in the treatment of the cancer.

It is contemplated that the invention has particular utility in the immunotherapy of human cancer, however, it is appreciated that the methodologies described herein may be applied to the treatment of cancers occurring in, for example, farm animals (i.e., cattle, horses, sheep, goats and pigs) and household pets (i.e., cats and dogs).

The main advantage this approach has over conventional methodologies is that it is not necessary to isolate and characterize the tumor specific antigen for each tumor. Once the stress protein-peptide complex has been isolated it is simply administered back the mammal without further characterization. Since the procedures for isolating the immunogenic complexes are routine and well known in the art, the artisan may rapidly and routinely prepare a specific immunogenic composition "tailor-made" for each individual being treated.

Another advantage of the instant method over previous methodologies is that the administration of purified stress protein-peptide complexes back to the individual from which they were derived eliminates the risk of inoculating the mammal undergoing therapy with potentially transforming agents (i.e., transforming DNA) and/or immunosuppressive agents which can be an issue when the complex is present in a biochemically undefined tumor or tumor extract. In addition, stress protein-peptide complexes can induce significant tumor immunity in the absence of adjuvants. Accordingly, while adjuvants may further enhance the immunotherapeutic properties of the complex, their availability is not a pre-condition for inducing a significant immune response.

It is contemplated that this method can be used in the treatment of a variety of tumors, for example, tumors that are mesenchymal in origin (sarcomas) i.e., fibrosarcomas; myxosarcomas; liposarcomas; chondrosarcomas; osteogenic sarcomas; angiosarcomas; endotheliosarcomas; lymphangiosarcomas; synoviosarcomas; mesotheliosarcomas; Ewing's tumors; myelogenous leukemias; monocytic leukemias; malignant lymphomas; lymphocytic leukemias; plasmacytomas; leiomyosarcomas and rhabdomyosarcoma.

In addition, it is contemplated that this method can be used in the treatment of tumors that are epithelial in origin (carcinomas) i.e., squamous cell or epidermal carcinomas; basal cell carcinomas; sweat gland carcinomas; sebaceous gland carcinomas; adenocarcinomas; papillary carcinomas; papillary adenocarcinomas; cystadenocarcinomas; medullary carcinomas; undifferentiated carcinomas (simplex carcinomas); bronchogenic carcinomas; bronchial carcinomas; melanocarcinomas; renal cell carcinomas; hepatocellular carcinomas; bile duct carcinomas; papillary carcinomas; transitional cell carcinomas; squamous cell carcinomas; choriocarcinomas; seminomas; embryonal carcinomas malignant teratomas and teratocarcinomas. Generic methodologies useful in the preparation of compositions effective at inducing an immune response against these tumors are discussed in detail herein below.

Although not wishing to be bound by theory, it is contemplated that the stress protein-peptide complexes stimulate an immune response against the tumor cells from which they are derived by means of a T cell cascade. Previous experiments have demonstrated that mice immunized prophylactically with stress protein-peptide preparations derived from a tumor originating in the-same strain of mouse or rat develop immunological resistance to the tumor from which it was isolated. The mice, however, fail to develop immunity against antigenically distinct tumors. Furthermore, stress protein-peptide complexes derived from normal tissues do not elicit resistance to any tumors tested. See for example, Srivastava et al. (1984) *Int. J. Cancer* 33:417; Srivastava et al. (1986) *Proc. Natl. Acad. Sci. USA* 83:3407; Palladino et al. (1987) *Cancer Res.* 47:5074; Feldweg et al. (1993) *J. Cell Biochem. Suppl.* 17D:108 (Abst.); Udono et al. (1993) *J. Cell. Biochem. Suppl.* 17D:113 and Udono (1993) *J. Exp. Med.* 178:1391–1396, the disclosures of which are incorporated herein by reference. Recently, it has been established prophylactic immunity typically is mediated by means of a T cell cascade, more specifically by means of a cytotoxic T cell cascade. See for example, Blachere et al. (1993) *J. Immunother.* 14:352–356, the disclosure of which is incorporated by reference herein. Accordingly, it is contemplated that the stress-protein complexes may also mediate their effect therapeutically by a similar mechanism; specifically, via a cytotoxic T cell cascade.

It is contemplated that the stress protein-peptide complexes typically will be isolated directly from tumor tissue excised from the mammal being treated. Under certain conditions, however, the amount of tumor tissue available for isolation of the complex may be limiting. Accordingly, it is contemplated that the excised tumor tissue may be proliferated using techniques well known in the art prior to the isolation of the stress protein-peptide complexes. For example, the excised tumor tissue may be proliferated either in vivo, for example, by transfecting a nude mouse with a sample of the tumor tissue, or in vitro, for example, by serially passaging the tumor cells in culture. The proliferated tumor tissue subsequently can be harvested and used as a starting material for the isolation of the stress protein-peptide complex.

Stress proteins useful in the practice of the instant invention may be defined as any cellular protein that satisfies the following criteria. It is a protein whose intracellular concentration increases when a cell is exposed to a stressful stimuli, is capable of binding other proteins or peptides, and is capable of releasing the bound proteins or peptides in the presence of adenosine triphosphate (ATP) or low pH.

The first stress proteins to be identified were the Hsp's which are synthesized in a cell in response to heat shock. To date, three major families of mammalian Hsp's have been identified and include Hsp60, Hsp70 and Hsp90 where the numbers reflect the approximate molecular weight of the stress proteins in kilodaltons. Many members of these families were found subsequently to be induced in response to other stressful stimuli including, but not limited to, nutrient deprivation, metabolic disruption, oxygen radicals, and infection with intracellular pathogens. See for example: Welch (May 1993) *Scientific American* 56–64; Young (1990) supra; Craig (1993) *Science* 260:1902–1903; Gething et al (1992) supra; and Lindquist et al. (1988) supra, the disclosures of which are incorporated herein by reference. It is contemplated that mammalian stress proteins belonging to all three families may be useful in the practice of the instant invention.

The major stress proteins accumulate to very high levels in stressed cells but occur at low to moderate levels in cells that have not been stressed. For example, the highly inducible mammalian Hsp70 is hardly detectable at normal temperatures but becomes one of the most actively synthesized proteins in the cell upon heat shock (Welch et al. (1985), *J. Cell. Biol.* 101:1198–1211). In contrast, Hsp90 and Hsp60 proteins are abundant at normal temperatures in most, but not all, mammalian cells and are further induced by heat (Lai et al. (1984), *Mol. Cell. Biol.* 4:2802–10; van Bergen en Henegouwen et al. (1987), *Genes Dev.*, 1:525–31).

Members of the mammalian Hsp90 family identified to date include cytosolic Hsp90 (also known as Hsp83) and the endoplasmic reticulum counterparts Hsp90 (also known as Hsp83), Hsp87, Grp94 (also known as ERp99) and gp96 (Gething et al. (1992) supra). Members of the Hsp70 family identified to date include: cytosolic Hsp70 (also known as p73) and Hsc70 (also known as p72), the endoplasmic reticulum counterpart BiP (also known as Grp78) and the mitochondrial counterpart Hsp 70 (also known as Grp75), Gething et al. (1992) supra. To date, members of the mammalian Hsp60 family have only been identified in the mitochondria, Gething et al. (1992) supra.

Stress proteins are among the most highly conserved proteins in existence. For example, DnaK, the Hsp70 from *E. coli* has about 50% amino acid sequence identity with Hsp70 proteins from eukaryotes (Bardwell et al. (1984) *Proc. Natl. Acad. Sci.* 81:848–852). The Hsp60 and Hsp90 families similarly exhibit high levels of intrafamilial conservation (Hickey et al. (1989) *Mol. Cell Biol.* 9:2615–2626; Jindal (1989) *Mol. Cell. Biol.* 9:2279–2283). In addition, it has been discovered that the Hsp60, Hsp70 and Hsp90 families are composed of proteins that are related to the stress proteins in sequence, for example, having greater than 35% amino acid identity, but whose expression levels are not altered by stress. Therefore it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression a levels in a cell are enhanced in response to a stressful stimulus.

The immunogenic stress protein-peptide complexes of the invention may include any complex containing a stress protein non covalently associated with a peptide that is capable of inducing an immune response in a mammal. Preferred complexes include, but are not limited to, Hsp70-peptide, Hsp90-peptide and gp96-peptide complexes. For example, the mammalian stress protein gp96 which is the endoplasmic reticulum counterpart of the cytosolic Hsp90 may be used in the practice of the instant invention.

Typical procedures for isolating stress protein-peptide complexes useful in the practice of the instant invention are set forth in detail below.

Purification of Hsp70-peptide Complexes

The purification of Hsp70-peptide complexes has been described previously, see for example, Udono et al. (1993) supra.

Initially, tumor cells are suspended in 3 volumes of 1×Lysis buffer consisting of 5 mM sodium phosphate buffer (pH7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 min and then homogenized in a dounce homogenizer until >95% cells are lysed.

Then the lysate is centrifuged at 1000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with phosphate buffered saline (PBS) containing 2 mM $Ca^{2+}$ and 2 mM $Mg^{2+}$. When the cells are lysed by mechanical shearing the supernatant is diluted with an equal volume of 2xLysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 min. Then the resulting supernatant is harvested and applied to a Mono Q FPLC column equilibrated in 20 mM Tris-Acetate pH 7.5, 20 mM NaCl, 0.1 mM EDTA and 15 mM 2-mercaptoethanol. The column is then developed with a 20 mM to 500 mM NaCl gradient and the eluted fractions fractionated by sodium dodecyl sulfate-polyacrylamide gel electrophoresis (SDS-PAGE) and characterized by immunoblotting using an appropriate anti-Hsp70 antibody (such as from clone N27F3-4, from StressGen).

Fractions strongly immunoreactive with the anti-Hsp70 antibody are pooled and the Hsp70 -peptide complexes precipitated with ammonium sulfate; specifically with a 50%–70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephadex$^R$ G25 column (Pharmacia).

The Hsp70-peptide complex can be purified to apparent homogeneity using this method. Typically 1 mg of Hsp70-peptide complex can be purified from 1 g of cells/tissue.

Purification of Hsp90-peptide Complexes

Initially, tumor cells are suspended in 3 volumes of 1xLysis buffer consisting of 5 mM sodium phosphate buffer (pH7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 min and then homogenized in a dounce homogenizer until >95% cells are lysed.

Then the lysate is centrifuged at 1000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with PBS containing 2 mM $Ca^{2+}$ and 2 mM $Mg^{2+}$. When the cells are lysed by mechanical shearing the supernatant is diluted with an equal volume of 2xLysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 min. Then the resulting supernatant is harvested and applied to a Mono Q FPLC column equilibrated equilibrated with lysis buffer. The proteins are then eluted with a a salt gradient of 200 mM to 600 mM NaCl.

The eluted fractions are fractionated by SDS-PAGE and fractions containing the Hsp90-peptide complexes identified by immunoblotting using a anti-Hsp90 antibody such as 3G3 (Affinity Bioreagents). Hsp90-peptide complexes can be purified to apparent homogeneity using this procedure. Typically, 150–200 μg of Hsp90-peptide complex can be purified from 1 g of cells/tissue.

Purification of gp96-peptide Complexes

Initially, tumor cells are suspended in 3 volumes of 1xLysis buffer consisting of 5mM sodium phosphate buffer (pH7), 150 mM NaCl, 2mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 min and then homogenized in a dounce homogenizer until >95% cells are lysed.

Then the lysate is centrifuged at 1000 g for 10 minutes to remove unbroken cells, nuclei and other cellular debris. The resulting supernatant is recentrifuged at 100,000 g for 90 minutes, the supernatant harvested and mixed with Con A Sepharose slurry equilibrated with PBS containing 2 mM $Ca^{2+}$ and 2 mM $Mg^{2+}$. When the cells are lysed by mechanical shearing the supernatant is diluted with an equal volume of 2xLysis buffer prior to mixing with Con A Sepharose. The supernatant is then allowed to bind to the Con A Sepharose for 2–3 hours at 4° C. The slurry is then packed into a column and washed with 1xlysis buffer until the $OD_{280}$ drops to baseline. Then the column is washed with 1/2 column bed volume of 10% α-methyl mannoside (α-MM), the column sealed with parafilm and incubated-at 37° C. for 15 min. The column is then cooled to room temperature, the parafilm removed from the bottom of the column, and five column volumes of a α-MM is applied to the column. The eluate is then fractionated and characterized by SDS-PAGE. Typically, the resulting gp96-peptide complex is about 60 to 95% pure depending upon the cell type and the tissue to lysis buffer ratio used.

If further purification is required, the sample can be applied to a Mono Q FPLC column equilibrated with a buffer containing 5mM sodium phosphate, pH7. The proteins are then eluted from the column with a 0–1M NaCl gradient. The gp96 fraction elutes between 400 mM and 550 mM NaCl.

As an alternative procedure, the gp96 fraction isolated from the 100,000 g pellet can be resuspended in 5 volumes of PBS containing 1% sodium deoxycholate (without $Ca^{2+}$ and $Mg^{2+}$) and incubated on ice for 1 h. The resulting suspension is centrifuged for 30 min at 20,000 g and the resulting supernatant harvested and dialyzed against several changes of PBS (without $Ca^{2+}$ and $Mg^{2+}$) to remove the detergent. The resulting dialysate is centrifuged for 90 min at 100,000 g and the supernatant purified further. Then calcium and magnesium are both added to the supernatant to give final concentrations of 2 mM. Then the sample is applied to a Mono Q HPLC column equilibrated with a buffer containing 5 mM sodium phosphate, pH7 and the proteins eluted with a 0–1M NaCl gradient. The gp96 fraction elutes between 400 mM and 550 mM NaCl.

The gp96-peptide complexes can be purified to apparent homogeneity using this procedure. Typically about 10–20 μg of gp96 can be isolated from 1 g cells/tissue using this method.

Formulation and Administration of the Complexes

Once stress protein-peptide complexes have been purified from the excised tumor they are administered back to the mammal undergoing therapy in order to stimulate in the mammal an immune response against tumor cells from which the complex was derived. The stress protein-peptide complexes of the invention may either be stored or prepared for administration by mixing with physiologically acceptable carriers, excipients, or stabilizers. These materials should be non-toxic to the intended recipient at dosages and concentrations employed.

When the complex is water soluble it may be formulated in an appropriate buffer, for example PBS (5 mM sodium phosphate, 150 mM NaCl, pH7.1) or other physiologically compatible solutions. Alternatively, if the resulting complex has poor solubility in aqueous solvents then it may be formulated with a non-ionic surfactant such as Tween, or polyethylene glycol.

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the stress protein-peptide complexes in vivo.

Formulations for inhalation may contain as excipients, for example, lactose. Aqueous solutions may contain, for example, polyoxyethylene-9-lauryl ether, glycocholate and deoxycholate. Oily solutions may be useful administration in the form of nasal drops. Gels may be applied topically intranasally.

The compounds provided herein can be formulated into pharmaceutical compositions by admixture with pharmaceutically acceptable nontoxic excipients and carriers. In addition the formulations may optionally contain one or more adjuvants. Preferred adjuvants include, but are not limited to, pluronic tri-block copolymers, muramyl dipeptide and its derivatives, detoxified endotoxin, saponin and its derivatives such as QS-21 and liposomes. The present invention further envisages sustained release formulations in which the complex is released over an extended period of time.

The mode of administration of the family of stress protein-peptide complexes prepared in accordance with the invention will necessarily depend upon the stability of the complex under physiological conditions, and the size and distribution of the tumor within the mammal being treated. The preferred dosage of complex to be administered also is likely to depend on such variables as the size and distribution of the tumor, the age, sex and weight of the intended recipient, the overall health status of the particular recipient, the relative biological efficacy of the complex, the formulation for the complex, the presence and types of excipients in the formulation, and the route of administration.

In general terms, the compounds of this invention may be provided in an aqueous physiological buffer solution containing about 0.001 to 10% w/v compound for parenteral administration. Preferred dosages range from about 1 to about 1000 micrograms of complex/kg body weight of recipient/administration and most preferably range from about 100 to about 250 micrograms of complex/kg body weight of recipient/administration. In particular, it is contemplated that a typical dose will range from about 5 mg to about 20 mg for a human subject weighing about 75 kg. These quantities, however, may vary according to the adjuvant coadministered with the complex.

The complex preferably comprises part of an aqueous solution which may be administered using standard procedures, for example, intravenously, subcutaneously, intramuscularly, intraorbitally, ophthalmically, intraventricularly, intracranially, intracapsularly, intraspinally, intracisternally, intraperitoneally, buccal, rectally, vaginally, intranasally or by aerosol administration. The aqueous solution preferably is physiologically acceptable so that in addition to delivery of the desired complex to the mammal, the solution does not otherwise adversely affect the mammal's electrolyte and/or volume balance. The aqueous medium for the complex thus may comprise normal physiologic saline (0.9% NaCl, 0.15M), pH 7–7.4 or other pharmaceutically acceptable salts thereof.

Preferably the recipient should be vaccinated three times at two week intervals. If necessary, the responses may be boosted at a later date by subsequent administration of the complex. It is contemplated that the optimal dosage and vaccination schedule may be determined empirically for each stress protein-peptide complex using techniques well known in the art.

Various cytokines, antibiotics, and other bioactive agents also may be coadministered with the stress protein-peptide complexes. For example, various known cytokines, i.e., interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interferon α (IFNα), interferon β (IFNβ), interferon γ (IFNγ), tumor necrosis factor α (TNF), tumor necrosis factor β (TNFβ), granulocyte colony stimulating factor (G-CSF), granulocyte/macrophage colony stimulating factor (GM-CSF), and transforming growth factor β (TGF-β) may be coadministered with the complexes in order to maximize the physiological response. However, it is anticipated that other but as yet undiscovered cytokines may be effective in the invention. In addition, conventional antibiotics may be coadministered with the stress protein-peptide complex. The choice of suitable antibiotics will however be dependent upon the disease in question.

EXAMPLE I

In this example, C57BL/6 and C3H mice approximately 100 g in weight, are purchased from Jackson Laboratories, Bar Harbor, Me. Malignant tumor cells are then injected subcutaneously into mice in order to induce experimental tumors in the mice. Specifically, malignant spindle cell carcinoma 6139 cells are injected subcutaneously into the C3H mice, malignant mouse Lewis lung carcinoma cells are injected subcutaneously into C57BL/6 mice and malignant mouse B16 melanoma cells are injected subcutaneously into C57BL/6 mice.

When the tumors have grown to a size such that they are both visible and palpable, a sample of the tumor tissue is excised. As a control, normal non malignant tissue is excised from some mice bearing the experimental tumors.

Then gp96-peptide, Hsp90-peptide and Hsp70-peptide complexes are isolated from both the excised normal and tumor derived tissues using the methods described hereinabove. Once isolated, the complexes are combined with PBS and administered back to the mice from which the complexes were derived. Usually 6 mice are tested in each experiment. The experiments are performed using the schedule set forth below:

| Experiment | Composition administered back to mice |
| --- | --- |
| 1 | gp96-peptide |
| 2 | Hsp70-peptide |
| 3 | Hsp90-peptide |
| 4 | gp96-peptide and Hsp70-peptide |
| 5 | gp96-peptide and Hsp90-peptide |
| 6 | Hsp70-peptide and Hsp90-peptide |
| 7 | Hsp70-peptide, Hsp90-peptide and gp96-peptide |
| 8 | buffer alone |

In one series of experiments the complexes are isolated from tumor cells whereas in a second series the complexes are isolated from normal cells. The mice are inoculated three times at weekly intervals with 20 micrograms (total weight) of the preselected complex(es). During therapy, the size of each tumor is measured daily. After 4 weeks the mice are sacrificed and the development of the tumor examined histologically. In addition, the sacrificed mice are examined for the presence or absence of metastasis.

It is expected that the tumors in mice treated with complexes derived from normal tissue will continue to grow and metastasize. In contrast, it is expected that the tumors in the mice treated with the complexes derived from the tumor tissue will be exhibit slower growth than the tumors in the control animals, and in some cases, it is expected that the tumor mass may get smaller and the tumor exhibit remission during therapy.

OTHER EMBODIMENTS

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An isolated population of stress protein-peptide complexes isolated from tumor cells of a household pet, wherein the peptide is noncovalently associated with the stress protein.

2. The isolated population of claim 1, wherein the tumor cell is from tumor tissue excised from the household pet.

3. The isolated population of claim 1, wherein the stress protein is hsp70.

4. The isolated population of claim 1, wherein the stress protein is hsp90.

5. The isolated population of claim 1, wherein the stress protein is gp96.

6. The isolated population of claim 1, wherein the stress protein-peptide complex is a combination of a hsp70-peptide complex, a hsp90-peptide complex, and a gp96-peptide complex.

7. The isolated population of claim 1, 2, 3, 4, 5 or 6, wherein the household pet is a dog.

8. The isolated population of claim 1, 2, 3, 4, 5 or 6, wherein the household pet is a cat.

9. An isolated stress protein-peptide complex isolated from a tumor cell of a household pet, wherein the peptide is noncovalently associated with the stress protein.

10. A composition comprising the isolated population of claim 1, 2, 3, 4, 5 or 6, and a pharmaceutically acceptable carrier.

11. The composition of claim 10, further comprising a cytokine.

12. A composition comprising the isolated population of claim 1, and a pharmaceutically acceptable carrier.

13. A composition comprising the isolated population of claim 7, and a pharmaceutically acceptable carrier.

14. A composition comprising the isolated population of claim 8, and a pharmaceutically acceptable carrier.

15. The composition of claim 12, further comprising a cytokine.

16. The composition of claim 13, further comprising a cytokine.

17. The composition of claim 14, further comprising a cytokine.

* * * * *